United States Patent
Nishizawa et al.

(10) Patent No.: US 8,742,179 B2
(45) Date of Patent: Jun. 3, 2014

(54) METHOD FOR PRODUCING ARYL, HETEROARYL, OR ALKENYL-SUBSTITUTED UNSATURATED HYDROCARBON

(75) Inventors: Toshiaki Nishizawa, Niigata-ken (JP); Makoto Funabora, Niigata-ken (JP)

(73) Assignee: Nippon Soda Co., Ltd., Tokyo (JP)

(*) Notice: Subject to any disclaimer, the term of this patent is extended or adjusted under 35 U.S.C. 154(b) by 227 days.

(21) Appl. No.: 13/390,312

(22) PCT Filed: Aug. 13, 2010

(86) PCT No.: PCT/JP2010/063781
§ 371 (c)(1),
(2), (4) Date: Feb. 13, 2012

(87) PCT Pub. No.: WO2011/021590
PCT Pub. Date: Feb. 24, 2011

(65) Prior Publication Data
US 2012/0142975 A1   Jun. 7, 2012

(30) Foreign Application Priority Data
Aug. 18, 2009 (JP) .................. 2009-188859

(51) Int. Cl.
*C07C 7/04* (2006.01)

(52) U.S. Cl.
USPC ............... 568/813; 568/810; 568/812

(58) Field of Classification Search
USPC ......................... 568/810, 812, 813
See application file for complete search history.

(56) References Cited

U.S. PATENT DOCUMENTS

| 4,540,833 | A  |    | 9/1985  | Wallace et al. |          |
|-----------|----|----|---------|----------------|----------|
| 7,300,639 | B2 |    | 11/2007 | Liu            |          |
| 8,314,090 | B2 | *  | 11/2012 | Howbert et al. | 514/213.01 |
| 8,354,528 | B2 | *  | 1/2013  | Babu et al.    | 544/121  |

FOREIGN PATENT DOCUMENTS

| JP | S56-079627 A | 6/1981  |
| JP | 63-273641    | 11/1988 |
| JP | 03-149228    | 6/1991  |
| JP | 04-225952    | 8/1992  |
| JP | 05-025163    | 2/1993  |
| JP | 05-039250    | 2/1993  |
| JP | 10-114691    | 5/1998  |
| JP | 2005-500392  | 1/2005  |
| JP | 2005-254092  | 9/2005  |
| JP | 2006-248943  | 9/2006  |
| JP | 2008-106354  | 5/2008  |
| WO | 03/018538    | 3/2003  |

OTHER PUBLICATIONS

Galaffu; Organic Process Research and Development, 2007, 11, 406-413.*
Office Action issued in the corresponding JP Appln. No. 2011-527663, dated Aug. 6, 2013, 6 pages (with English translation).
International Search Report for PCT/JP2010/063781, dated Oct. 26, 2010, 2 pages.
Konigsberger, Kurt, et al., "A Practical Synthesis of 6-[2-(2,5-Dimethoxyphenyl)ethyl]-4-ethylquinazoline and the Art of Removing Palladium from the Products of Pd-Catalyzed Reactions", Organic Process Research & Development, 2003, vol. 7, pp. 733-742.
Flahive, Erik J., et al., "Development of an Effective Palladium Removal Process for VEGF Oncology Candidate AG13736 and a Simple, Efficient Screening Technique for Scavenger Reagent Identification", Organic Process Research & Development, 2008, vol. 12, pp. 637-645.

* cited by examiner

*Primary Examiner* — Sudhakar Katakam
*Assistant Examiner* — Pancham Bakshi
(74) *Attorney, Agent, or Firm* — Kenyon & Kenyon, LLP

(57) ABSTRACT

The present invention relates to a method for producing aryl-, heteroaryl- or alkenyl-substituted unsaturated hydrocarbons, containing: reacting aryl halides, heteroaryl halides or alkenyl halides with alkynes or alkenes in the presence of a palladium catalyst to obtain a crude product, and subsequently distillatively purifying the crude product in the presence of a compound having at least one NC=S group.

5 Claims, No Drawings

METHOD FOR PRODUCING ARYL, HETEROARYL, OR ALKENYL-SUBSTITUTED UNSATURATED HYDROCARBON

TECHNICAL FIELD

The present invention relates to a method for industrially producing aryl-, heteroaryl- or alkenyl-substituted unsaturated hydrocarbons in a high yield by a coupling reaction of aryl halides, heteroaryl halides or alkenyl halides with alkynes or alkenes by using a palladium catalyst.

BACKGROUND ART

The aryl-, heteroaryl- or alkenyl-substituted unsaturated hydrocarbons are useful as a physiological active substance (e.g., medicine, agrichemical), a functional material (e.g., liquid crystal material, electronic material, optical material, photographic additive, thermosetting resin), or a synthetic intermediate thereof (see, for example, Patent Documents 6 to 9).

The aryl- or alkenyl-substituted unsaturated hydrocarbons are obtained, for example, by reacting aryl halides or alkenyl halides with alkynes or alkenes in the presence of a palladium catalyst (so-called Sonogashira coupling or Mizoroki-Heck reaction).

As for the production method of aryl- or alkenyl-substituted unsaturated hydrocarbons by Sonogashira coupling, a large number of proposals have been made. For example, Patent Document 1 discloses a method of reacting an aromatic halide and an acetylene compound in the presence of a palladium catalyst, a copper salt, a base and a compound capable of releasing a halogen ion, subsequently adding dilute hydrochloric acid and an organic solvent to effect liquid separation, and purifying the organic phase by silica gel column chromatography to produce an aromatic acetylene compound.

Patent Document 2 discloses a method of performing a coupling reaction of alkynes having a methine group at the terminal and an organic compound having a leaving group such as halogen group in the presence of a catalyst containing a transition metal element such as palladium, an inorganic salt, and a ligand such as triarylphosphine or iminophosphine compound, subsequently separating the product from the reaction mixture by using high-performance liquid chromatography for sampling, and purifying the product by using gel permeation chromatography to obtain the objective coupling reaction product.

In the production methods described in Patent Documents 1 and 2, purification by extraction and chromatography is employed, but chromatography is unsuited for mass production.

Patent Document 3 discloses a production method of phenylalkynes, comprising steps of reacting a halophenol and an acetylene compound in the presence of an amine solvent, a palladium complex catalyst and a copper salt, adding dilute hydrochloric acid to the obtained reaction mixture to effect liquid separation and remove hydrogen chloride, subsequently adding an amino compound capable of forming a complex with palladium and copper, and removing the produced palladium complex and copper complex. Patent Document 5 discloses a method for synthesizing an acetylene compound having a nitrogen-containing aromatic group by a reaction of ethynylpyridines and haloaryls in the presence of a palladium catalyst and a copper catalyst. In the production methods described in Patent Documents 3 and 5, extraction for purification is employed.

Patent Document 4 discloses a method for producing an arylalkyne compound by reacting an aryl halide such as iodotoluene with an amino group-containing acetylene compound such as N-(2-propynyl)piperidine in the presence of a palladium catalyst, a base and a copper(I) salt, subsequently removing the solvent under reduced pressure, washing the residue, and finally performing distillative purification. In the production method described in Patent Document 4, distillation for purification is employed.

RELATED ART

Patent Document

Patent Document 1: JP-A-10-114691
Patent Document 2: JP-A-2005-254092
Patent Document 3: U.S. Pat. No. 4,540,833
Patent Document 4: JP-T-2005-500392
Patent Document 5: JP-A-2006-248943
Patent Document 6: WO2003/018538
Patent Document 7: JP-A-5-25163
Patent Document 8: JP-A-5-39250
Patent Document 9: JP-A-4-225952

SUMMARY OF THE INVENTION

Problems that the Invention is to Solve

Distillation is a very effective method as the method for industrially isolating and purifying a product. It is suitable for industrial mass production to distillatively purify a coupling reaction product of aryl halides, heteroaryl halides or alkenyl halides with alkynes or alkenes as in the production method described in Patent Document 4. According to the studies by the present inventors, aryl-, heteroaryl- or alkenyl-substituted unsaturated hydrocarbon could be obtained in a high yield by distillative purification on a small scale. However, when distillative purification is performed on a large scale commensurate with industrial production, the yield of aryl-, heteroaryl- or alkenyl-substituted unsaturated hydrocarbons was sometimes greatly reduced.

An object of the present invention is to provide a method capable of producing aryl-, heteroaryl- or alkenyl-substituted unsaturated hydrocarbons (that is, arylalkynes, arylalkenes, heteroarylalkynes, heteroarylalkenes, alkenylalkynes or alkenylalkenes) by a coupling reaction between aryl halides, heteroaryl halides or alkenyl halides and alkynes or alkenes with use of a palladium catalyst, in a high yield even for industrial large-scale production.

Means for Solving the Problems

The present inventors have made intensive investigations to attain the above-described object, as a result, it has been discovered that in the distillative purification for large-scale production, the product is heated at a higher temperature for a longer time than in the small-scale production and when a palladium catalyst or a decomposition product thereof remains in this heated state, the coupling reaction product is decomposed.

Then, the present inventors have found that when distillative purification is performed in the presence of sodium diethyldithiocarbamate, decomposition of the product is inhibited and reduction in the yield is suppressed. Furthermore, the present inventors have found that reduction in the yield can be suppressed not only in case of sodium diethyldithiocarbamate but also in case of using its generalized compound, that is, a compound having at least one NC=S group. The present invention has been accomplished based on these findings.

That is, the present invention is a method for producing aryl-, heteroaryl- or alkenyl-substituted unsaturated hydrocarbons, comprising reacting aryl halides, heteroaryl halides or alkenyl halides with alkynes or alkenes in the presence of a palladium catalyst to obtain a crude product, and subsequently distillatively purifying the crude product in the presence of a compound having at least one NC=S group.

Advantage of the Invention

According to the present invention, aryl-, heteroaryl- or alkenyl-substituted unsaturated hydrocarbons can be produced by a coupling reaction between aryl halides, heteroaryl halides or alkenyl halides and alkynes or alkenes with use of a palladium catalyst, in a high yield even for industrial large-scale production.

The reason for offering such an effect is not clearly known but can be presumed as follows. The compound having at least one NC=S group, such as dithiocarbamates and thioureas, is known to coordinate to palladium and produce a solvent-insoluble palladium complex (U.S. Pat. No. 7,300,639). It is considered from this knowledge that palladium derived from the residual palladium catalyst or a decomposition product thereof in the product solution subjected to distillative purification is converted into a solvent-insoluble palladium complex by the compound having at least one NC=S group, as a result, the reaction activity of palladium is reduced and even when the product is heated at a high temperature for a long time, its decomposition reaction does not proceed any more.

Mode for Carrying Out the Invention

The method for producing aryl-, heteroaryl- or alkenyl-substituted unsaturated hydrocarbons of the present invention comprises reacting aryl halides, heteroaryl halides or alkenyl halides with alkynes or alkenes in the presence of a palladium catalyst to obtain a crude product, and distillatively purifying the crude product in the presence of a compound having at least one NC=S group.

The aryl halides and heteroaryl halides for use in the present invention are an aromatic compound and a heteroaromatic compound, which are substituted with at least one halogen atom (leaving group). Here, the aromatic compound and heteroaromatic compound are a compound containing a ring having (4n+2) (wherein n represents a natural number) π-electrons. Accordingly, the aromatic compound includes benzene, naphthalene or the like. The heteroaromatic compound is a compound having an aromatic ring containing a heteroatom selected from a nitrogen atom, a sulfur atom, an oxygen atom and the like, that is, includes, for example, pyridine, pyrimidine, pyrrole, indole, thiophene, or furan. The aryl halides and heteroaryl halides are preferably an aromatic compound and a heteroaromatic compound, where at least one halogen atom (leaving group) is bonded to the $sp^2$ carbon.

The alkenyl halides for use in the present invention are an alkene compound where at least one halogen atom (leaving group) is bonded to the $sp^2$ carbon. Examples of the non-halogen-substituted alkene compound include ethylene, propylene, 1-butene, 2-butene, 1-heptene, 2-heptene and cyclohexene.

The halogen atom includes a fluorine atom, a chlorine atom, a bromine atom and an iodine atom. As for the halogen atom substituted on, a halogen atom having a larger atomic weight is higher in the activity for a coupling reaction. For example, in case of an aromatic compound substituted with 3 fluorine atoms and 1 chlorine atom, the coupling reaction is liable to occur in the chlorine atom moiety.

The aryl halides, heteroaryl halides and alkenyl halides for use in the present invention may have a substituent other than a halogen atom.

Examples of the substituent other than a halogen atom include an alkyl group such as methyl group and ethyl group; an aryl group such as phenyl group and naphthyl group; a cyano group; a carboxyl group; an alkoxycarbonyl group such as methoxycarbonyl group; an aryloxycarbonyl group such as phenoxycarbonyl group; a carbamoyl group; a substituted carbamoyl group such as N-phenylcarbamoyl group and N,N-dimethylcarbamoyl group; an alkylcarbonyl group such as acetyl group; an arylcarbonyl group such as benzoyl group; a nitro group; an amino group; a substituted amino group such as dimethylamino group and anilino group; an acylamino group such as acetamide group and ethoxycarbonylamino group; a sulfonamide group such as methanesulfonamide group; an imide group such as succinimide group and phthalimide group; an imino group such as benzylideneamino group; a hydroxy group; an alkoxy group such as methoxy group; an aryloxy group such as phenoxy group; an acyloxy group such as acetoxy group; an alkylsulfonyloxy group such as methanesulfonyloxy group; an arylsulfonyloxy group such as benzenesulfonyloxy group; a sulfo group; a sulfamoyl group; a substituted sulfamoyl group such as N-phenylsulfamoyl group; an alkylthio group such as methylthio group; an arylthio group such as phenylthio group; an alkylsulfonyl group such as methanesulfonyl group; and an arylsulfonyl group such as benzenesulfonyl group.

When an electron-attracting substituent is bonded as the substituent other than a halogen atom, the coupling reactivity is greatly increased. Examples of the electron-attracting substituent include a halogen atom different from the halogen atom participating in the coupling reaction, a cyano group, an alkoxycarbonyl group, an aryloxycarbonyl group, a substituted or unsubstituted carbamoyl group, an alkylcarbonyl group, an arylcarbonyl group, a nitro group, a substituted or unsubstituted sulfamoyl group, an alkylsulfonyl group, and an arylsulfonyl group.

The alkynes for use in the present invention are a compound having sp carbon. Examples thereof include a compound having a methine group at the terminal (for example, can be represented by formula I: $R^1\!\equiv\!CH$ (wherein $R^1$ represents an organic group or a hydrogen atom)), and an organic metal compound having a terminal methine group substituted with a metal such as zinc and tin (for example, can be represented by formula II: $R^1\!\equiv\!CM$ (wherein $R^1$ represents an organic group or a hydrogen atom, and M represents a metal element-containing group)). Among these, the production method of the present invention is preferably applied to alkynes having a hydrogen atom on the α-position of the alkyne bond.

The alkenes for use in the present invention are a compound having $sp^2$ carbon. Examples of the alkenes include a compound having an ethenyl group at the terminal (for example, can be represented by formula III: $R^1{}_2C\!=\!CH_2$ (wherein each of two $R^1$s independently represents an organic group or a hydrogen atom)). Specific examples thereof include ethylene, propylene, 1-butene, 1-heptene and 1-hexene. In the Mizoroki-Heck reaction, a compound having an ethenyl group at the terminal is preferably used.

In formulae I, II and III, examples of the organic group represented by $R^1$ include an aliphatic hydrocarbon group such as alkyl group (e.g., methyl group, ethyl group, propyl group, butyl group, and tert-butyl group) and alkenyl group (e.g., vinyl group, propenyl group, allyl group, and butenyl group); an alicyclic hydrocarbon group such as cycloalkyl group (e.g., cyclohexyl group, and cyclooctyl group), cycloalkenyl group (e.g., cyclohexenyl group), cycloalkadienyl group (e.g., cyclohexedienyl group), cycloalkylalkyl group (e.g., cyclohexylmethyl group), cycloalkenylalkyl group (e.g., cyclohexenylmethyl group) and cycloalkadienylalkyl group (e.g., cyclohexadienylmethyl group); and an aromatic hydrocarbon group such as aryl group (e.g., phenyl group, and naphthyl group) and aralkyl group (e.g., benzyl group, and phenethyl group). These hydrocarbon groups may have an unsaturated bond such as double bond or triple bond in the molecule or may have a heteroatom (for example, O, N, S, P, Sn, B or Si atom).

The hydrocarbon group above may have a substituent such as hydroxyl group, alkoxy group, aryloxy group, acyl group, carboxyl group, alkoxycarbonyl group, aryloxycarbonyl group, amino group, N-substituted amino group, nitro group, cyano group and halogen atom.

In formula II, examples of the metal element-containing group represented by M include chlorozinc (ClZn—), trimethyltin (($CH_3$)$_3$Sn—) and tributyltin ($C_4H_9$)$_3$Sn—).

In the coupling reaction of aryl halides, heteroaryl halides or alkenyl halides with alkynes or alkenes, the methine group or metal-substituted terminal methine group in the alkynes or the ethenyl group in the alkenes is preferably used in a ratio to account for 0.7 to 1.3 mol per mol of the leaving group in the aryl halides, heteroaryl halides or alkenyl halides.

As the palladium catalyst, a known catalyst for use in the Sonogashira coupling or Mizoroki-Heck reaction can be used. For example, a palladium compound such as 0-valent or divalent palladium metal or a salt (including a complex) thereof may be used. The palladium catalyst may be supported on a support such as activated carbon. Examples of the palladium compound which is preferably used include palladium (0)/carbon, palladium(II) acetate, palladium(II) chloride, palladium(II) acetylacetonate, bis(triphenylphosphine)palladium(II) chloride, tris(dibenzylideneacetone)dipalladium(0), tetrakis(triphenylphosphine)palladium(0), $PdCl_2(PPh_3)_2$, and $Pd(OAc)_2 \cdot (PPh_3)_2$ (incidentally, Ph represents a phenyl group, and OAc represents an acetoxy group). Among these, tetrakis(triphenylphosphine)palladium(0) is particularly preferably used. The palladium catalyst is used in an amount of preferably from 0.001 mmol to 1 mol, more preferably from 0.01 mmol to 0.01 mol, and still more preferably from 0.01 mmol to 0.05 mol, per mol of the aryl halides, heteroaryl halides or alkenyl halides.

In the present invention, a monovalent or divalent copper salt, preferably a monovalent copper salt, may be used together with the palladium catalyst. Of copper salts, copper (I) chloride is preferred. The copper salt can be used in an amount of preferably from 0.1 mmol to 0.1 mol per mol of the aryl halides, heteroaryl halides or alkenyl halides.

In the present invention, the reaction can be performed by adding a phosphine-based ligand together with the palladium catalyst. Examples of the phosphine-based ligand include triarylphosphine, diarylalkylphosphine, aryldialkyphosphine, trialkylphosphine and iminophosphine. Among these, triphenylphosphine is preferred. A bidentate ligand having two phosphorus atoms in the molecule may be also used. The phosphine-based ligand can be used in an amount of preferably from 0.1 mmol to 0.1 mol per mol of the aryl halides, heteroaryl halides or alkenyl halides.

In the present invention, the reaction is preferably performed by further adding a base. Examples of the base which can be used include sodium hydroxide, sodium carbonate, sodium hydrogencarbonate, potassium hydroxide, potassium carbonate, potassium hydrogencarbonate, sodium hydride, sodium methoxide, sodium ethoxide, sodium tert-butoxide, potassium tert-butoxide, and an organic base such as triethylamine, diethylamine, piperidine, pyrrolidine, 1,8-diazabicyclo[5.4.0]-7-undecene (DBU) and pyridine. Among these, an organic base is preferred, and triethylamine and diethylamine are particularly preferred. The base can be used in an amount of preferably from 1 to 100 mol, more preferably from 1 to 10 mol, per mol of the aryl halides, heteroaryl halides or alkenyl halides. The base can trap a hydrogen halide that is a by-product.

Usually, an organic solvent is used as the reaction solvent. Examples of the reaction solvent which is preferably used include an aromatic hydrocarbon-based solvent such as toluene, an amide-based solvent such as acetonitrile, N,N-dimethylacetamide and N,N-dimethylformamide, an ether-based solvent such as tetrahydrofuran, and pyridine. Among these, an amide-based solvent with good solubility is preferably used. In the case where the solubility of alkynes or alkenes and aryl halides, heteroaryl halides or alkenyl halides is low, tetrahydrofuran or the like may be added as an auxiliary solvent to make a mixed solvent.

The temperature during the coupling reaction is usually from 0 to 150° C., preferably from 20 to 130° C., more preferably from 20 to 110° C. The reaction may be performed under an air atmosphere but usually, is preferably performed under an inert gas atmosphere. Examples of the inert gas include a rare gas such as argon and helium; and a nitrogen gas. The pressure during the reaction may be appropriately selected according to the kinds of aryl halides, heteroaryl halides or alkenyl halides and alkynes or alkenes, and is usually from 0.0001 to 100 MPa, preferably from 0.001 to 10 MPa, more preferably from 0.01 to 1 MPa.

In the present invention, before distillatively purifying the crude product obtained in the coupling reaction above, solvent extraction can be performed. The extraction conditions are not particularly limited as long as impurities such as catalyst can be removed. For example, first, an acid such as dilute hydrochloric acid (an aqueous solution of hydrogen chloride) and an organic solvent such as methylcyclohexane are added to the crude product obtained in the coupling reaction to thereby perform extraction. Water is added to the organic phase obtained in the extraction above to thereby perform extraction. To the organic phase resulting from this extraction, a base such as aqueous sodium hydrogencarbonate solution and aqueous ammonia is added to perform extraction. Furthermore, an aqueous sodium chloride solution is added to the organic phase resulting from the extraction above to thereby perform extraction. Finally, the solvent is, for example, evaporated from the organic phase obtained by the extraction, whereby the concentration is adjusted to that suitable for distillative purification.

In the present invention, the crude product obtained in the coupling reaction above or the crude product after a solvent extraction treatment thereof is distillatively purified. The distillative purification must be performed in the presence of a compound having at least one NC=S group. The concentration method involving heating at a high temperature is also preferably performed in the presence of a compound having at least one NC=S group.

Examples of the compound having at least one NC=S group include dithiocarbamic acid and its salts, thioureas, O-alkyl thiocarbamates, thiuram monosulfides, and thiuram disulfides. Among these, dithiocarbamates and thioureas are preferred.

Examples of the dithiocarbamates include zinc dimethyldithiocarbamate, sodium dimethyldithiocarbamate, bismuth dimethyldithiocarbamate, calcium dimethyldithiocarbamate, copper dimethyldithiocarbamate, lead dimethyldithiocarbamate, selenium dimethyldithiocarbamate, sodium diethyldithiocarbamate, ammonium diethyldithiocarbamate, copper diethyldithiocarbamate, lead diethyldithiocarbamate, selenium diethyldithiocarbamate, tellurium diethyldithiocarbamate, zinc dibutyldithiocarbamate, sodium dibutyldithiocarbamate, dibutyl ammonium dibutyldithiocarbamate, zinc dibenzyldithiocarbamate, zinc methylphenyl dithiocarbamate, zinc ethylphenyl dithiocarbamate, zinc pentamethylene dithiocarbamate, calcium pentamethylene dithiocarbamate, lead pentamethylene dithiocarbamate, sodium pentamethylene dithiocarbamate, and piperidine pentamethylene dithiocarbamate. The dithiocarbamate is preferably a sodium salt.

Examples of the thioureas include thiourea, 1,3-dimethylthiourea, 1,3-diethyl-2-thiourea, 1-acetyl-2-thiourea, 1-allyl-3-(2-hydroxyethyl)-2-thiourea, 1-amidino-2-thiourea, 1,3-diethylthiourea, 1,3-diphenylthiourea, 1,3-dibutylthiourea, 1,3-dimethylthiourea, tributylthiourea, trimethylthiourea, 1,3-bis(dimethylaminopropyl)-2-thiourea, tetramethylthiourea, and N-methylthiourea.

The compound having at least one NC=S group is used in an amount of preferably from 0.1 to 2 mol %, more preferably from 0.2 to 0.5 mol %, based on the aryl-, heteroaryl- or alkenyl-substituted unsaturated hydrocarbons contained in the crude product before distillation. If the amount of the compound having at least one NC=S group is too small, the yield of aryl-, heteroaryl- or alkenyl-substituted unsaturated hydrocarbons is liable to decrease. If the amount of the compound having at least one NC=S group is excessively large, the reduction reaction (hydrogenation reaction) or cyclization reaction using, as the raw material, the aryl-, heteroaryl- or alkenyl-substituted unsaturated hydrocarbons obtained by the distillative purification tends to be suppressed from proceeding.

The method for distillation is not particularly limited, but in the present invention, distillation under reduced pressure is preferred. By performing distillation under reduced pressure, evaporation can be accelerated while keeping the aryl-, heteroaryl- or alkenyl-substituted unsaturated hydrocarbons from being overheated.

The distillation apparatus applicable to the present invention is not particularly limited, and examples thereof include a simple distillation apparatus, a shelf plate tower and a packed tower. The distillation temperature and distillation time can be appropriately determined according to, for example, the boiling point of the aryl-, heteroaryl- or alkenyl-substituted unsaturated hydrocarbons obtained in the reaction above, the boiling point of the compound having at least one NC=S group added, or the boiling point of the solvent.

EXAMPLES

The present invention is specifically described below by referring to Examples and Comparative Examples, but the present invention is not limited to these Examples. Unless otherwise indicated, the parts and % are on the mass basis.

In Examples and Comparative Examples, the concentration of the target in the crude product was determined by HPLC analysis.

Conditions of HPLC Analysis

Column: Waters Symmetry $C_{18}$ 5 μm 4.6×150 mm
Temperature: 50° C.
Flow rate: 1 mL/min
Wavelength: 245 nm
Mobile phase composition: MeCN:$H_2O$:10% $H_3PO_4$=550:450:1
Internal standard: benzophenone
Also, identification of the target was performed by $^1$H-NMR analysis.

Example 1

A reaction vessel was charged with 82.43 g of bromobenzene, and 250 ml of N,N-dimethylformamide and 84.7 g of triethylamine were added thereto. The inside of the reaction vessel was purged with nitrogen.

Subsequently, 2.3 g of tetrakis(triphenylphosphine)palladium and 1 g of copper(I) chloride were added, and the temperature was elevated to 100° C. While keeping the temperature at 100° C., 34.06 g of 1-pentyne was added dropwise over 2 hours. After the completion of dropwise addition, stirring was performed further for 2 hours while keeping the temperature at 100° C. The obtained solution was cooled to room temperature, and 335 ml of 10% hydrochloric acid was added. This mixture was stirred for 30 minutes and then extracted with methylcyclohexane. Water was added to the obtained organic phase to thereby perform extraction. Furthermore, an aqueous 4% sodium hydrogencarbonate solution was added to the obtained organic phase to thereby perform extraction. Subsequently, an aqueous 10% sodium chloride solution was added to the obtained organic phase to thereby perform extraction. Finally, the solvent was removed by distillation from the obtained organic phase to obtain Crude Product (I).

Crude Product (I) obtained above and sodium N,N-diethyldithiocarbamate trihydrate in a ratio to account for 1 mol % based on 1-phenyl-1-pentyne contained in Crude Product (I) were charged into a flask equipped with a reflux vessel and after elevating the temperature to 160° C., the contents were heated at 160° C. for 120 minutes under normal pressure. The obtained solution was cooled to room temperature and then subjected to distillation under reduced pressure at a temperature of about 96° C. and a pressure of 1.0 mmHg. The yield of 1-phenyl-1-pentyne was 64.9%.

Comparative Example 1

Crude Product (I) was obtained in the same manner as in Example 1. Crude Product (I) was charged into a flask equipped with a reflux vessel and after elevating the temperature to 160° C., heated at 160° C. for 120 minutes under normal pressure. The obtained solution was cooled to room temperature and then subjected to distillation under reduced pressure at a temperature of about 96° C. and a pressure of 1.0 mmHg. The yield of 1-phenyl-1-pentyne was 50.3%.

Example 2

Crude Product (II) was obtained in the same manner as in Example 1 except that 34.06 g of 1-pentyne was changed to 42.06 g of 1-pentyne-3-ol, and it was subjected to heating and distillation in the same manner as in Example 1. The yield of 1-phenyl-1-pentyne-3-ol was 58.0%.

Comparative Example 2

Crude Product (II) was obtained in the same manner as in Example 1 except that 34.06 g of 1-pentyne was changed to 42.06 g of 1-pentyne-3-ol, and it was subjected to heating and distillation in the same manner as in Comparative Example 1. The yield of 1-phenyl-1-pentyne-3-ol was 10.9%.

Example 3

Crude Product (III) was obtained in the same manner as in Example 1 except that 34.06 g of 1-pentyne was changed to 42.06 g of 1-pentyne-4-ol, and it was subjected to heating and distillation in the same manner as in Example 1. The yield of 1-phenyl-1-pentyne-4-ol was 63.2%.

Comparative Example 3

Crude Product (III) was obtained in the same manner as in Example 1 except that 34.06 g of 1-pentyne was changed to 42.06 g of 1-pentyne-4-ol, and it was subjected to heating and distillation in the same manner as in Comparative Example 1. The yield of 1-phenyl-1-pentyne-4-ol was 10.0%.

Example 4

Crude Product (IV) was obtained in the same manner as in Example 1 except that 34.06 g of 1-pentyne was changed to 42.06 g of 2-methyl-3-butyne-2-ol, and it was subjected to heating and distillation in the same manner as in Example 1. The yield of 1-phenyl-3-methyl-1-butyne-3-ol was 57.2%.

Comparative Example 4

Crude Product (IV) was obtained in the same manner as in Example 1 except that 34.06 g of 1-pentyne was changed to 42.06 g of 2-methyl-3-butyne-2-ol, and it was subjected to heating and distillation in the same manner as in Comparative Example 1. The yield of 1-phenyl-3-methyl-1-butyne-3-ol was 53.8%.

As mentioned above, it is seen that in the case where a compound having at least one NC=S group, such as dithiocarbamate or thioureas, is added to the coupling reaction product of aryl halides, heteroaryl halides or alkenyl halides with alkynes or alkenes, even when extra heat is added by heating under normal pressure and then distillative purification is performed, the coupling reaction product remains without undergoing decomposition, and the yield is high. On the other hand, in the case of not adding a compound having an NC=S group, the coupling reaction product is decomposed due to heat in the heating under normal pressure and the distillative purification, and the yield is decreased.

While the invention has been described in detail and with reference to specific embodiments thereof, it will be apparent to one skilled in the art that various changes and modifications can be made therein without departing from the spirit and scope of the invention.

This application is based on Japanese Patent Application No. 2009-188859 filed on Aug. 18, 2009, the contents of which are incorporated herein by way of reference.

The invention claimed is:

1. A method for producing aryl-, heteroaryl- or alkenyl-substituted unsaturated hydrocarbons, comprising:
   reacting aryl halides, heteroaryl halides or alkenyl halides with alkynes or alkenes in the presence of a palladium catalyst to obtain a crude product, and subsequently
   distillatively purifying said crude product in the presence of a compound having at least one NC=S group.

2. The method for producing aryl-, heteroaryl- or alkenyl-substituted unsaturated hydrocarbons according to claim 1, wherein the compound having at least one NC=S group is dithiocarbamates or thioureas.

3. The method for producing aryl-, heteroaryl- or alkenyl-substituted unsaturated hydrocarbons according to claim 1, wherein extraction with solvent is performed after the reaction of aryl halides, heteroaryl halides or alkenyl halides with alkynes or alkenes but before said distillative purification.

4. The method for producing aryl-, heteroaryl- or alkenyl-substituted unsaturated hydrocarbons according to claim 1, wherein the compound having at least one NC=S group is used in an amount of 0.1 to 2 mol % based on aryl-, heteroaryl- or alkenyl-substituted unsaturated hydrocarbons contained in the crude product before distillation.

5. The method for producing aryl-, heteroaryl- or alkenyl-substituted unsaturated hydrocarbons according to claim 1, wherein the compound having at least one NC=S group is used in an amount of 0.2 to 0.5 mol % based on aryl-, heteroaryl- or alkenyl-substituted unsaturated hydrocarbons contained in the crude product before distillation.

* * * * *